(12) United States Patent
Kuang

(10) Patent No.: US 9,791,529 B2
(45) Date of Patent: Oct. 17, 2017

(54) METHOD AND DEVICE FOR INDICATING DIFFERENTIATION BETWEEN TISSUES

(71) Applicant: Siemens Aktiengesellschaft, Munich (DE)

(72) Inventor: Bin Kuang, Shenzhen (CN)

(73) Assignee: Siemens Aktiengesellschaft, Munich (DE)

( * ) Notice: Subject to any disclaimer, the term of this patent is extended or adjusted under 35 U.S.C. 154(b) by 125 days.

(21) Appl. No.: 14/587,085

(22) Filed: Dec. 31, 2014

(65) Prior Publication Data

US 2015/0186606 A1 Jul. 2, 2015

(30) Foreign Application Priority Data

Dec. 31, 2013 (CN) .......................... 2013 1 0753430

(51) Int. Cl.

| | |
|---|---|
| *G01N 33/48* | (2006.01) |
| *G01N 33/50* | (2006.01) |
| *G01R 33/50* | (2006.01) |
| *G06F 17/10* | (2006.01) |
| *G06F 19/18* | (2011.01) |
| *G06F 17/11* | (2006.01) |
| *G06F 19/12* | (2011.01) |
| *A61B 5/055* | (2006.01) |
| *A61B 5/00* | (2006.01) |
| *G01R 33/56* | (2006.01) |

(52) U.S. Cl.
CPC .............. *G01R 33/50* (2013.01); *A61B 5/055* (2013.01); *A61B 5/7246* (2013.01); *G06F 17/10* (2013.01); *G06F 17/11* (2013.01); *G06F 19/12* (2013.01); *G06F 19/18* (2013.01); *A61B 5/7264* (2013.01); *G01R 33/5608* (2013.01)

(58) Field of Classification Search
None
See application file for complete search history.

(56) References Cited

U.S. PATENT DOCUMENTS 6,706,036 B2 * 3/2004 Lai ..................... B23K 26/0624
606/12
7,026,121 B1 * 4/2006 Wohlgemuth ....... C12Q 1/6883
435/6.1

OTHER PUBLICATIONS

Golub et al. Molecular classification of cancer: Class discovery and class prediction by gene expression monitoring. Science, vol. 286, 1999, pp. 531-537.*

* cited by examiner

*Primary Examiner* — Russell S Negin
(74) *Attorney, Agent, or Firm* — Schiff Hardin LLP

(57) ABSTRACT

The present invention provides a method for indicating differentiation between tissues. For each tissue amongst multiple tissues, a magnetization vector corresponding to each tissue is generated on the basis of a random scan sequence; on the basis of the magnetization vector corresponding to each of the multiple tissues, a differentiation-indicating value between each pair of the multiple tissues is calculated. Thus, a physician can select a suitable random scan sequence, according to the method provided in the present invention, and generate a magnetic resonance image comprising multiple brightness curves corresponding to multiple tissues, such that the trends of the brightness curves corresponding to the multiple tissues in the magnetic resonance image differ significantly. The present invention also provides a device for indicating differentiation between tissues.

20 Claims, 4 Drawing Sheets

*FIG. 5*
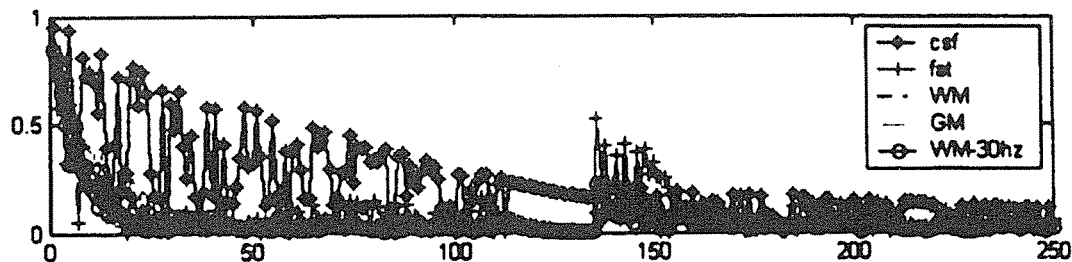
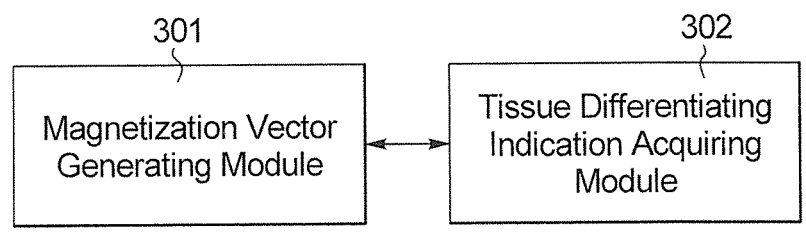
*FIG. 6*
*FIG. 7*
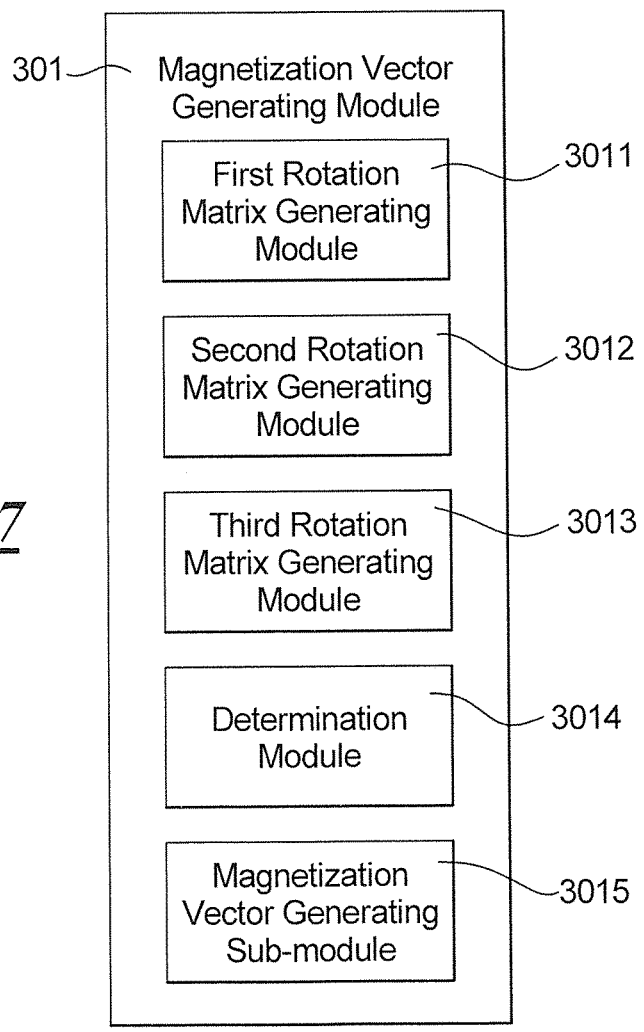

METHOD AND DEVICE FOR INDICATING DIFFERENTIATION BETWEEN TISSUES

BACKGROUND OF THE INVENTION

Field of the Invention

The present invention relates to the field of magnetic resonance, in particular to a method and device for indicating differentiation between tissues.

Description of the Prior Art

Magnetic resonance technology is a powerful measurement technology with many uses. Magnetic resonance imaging (MRI) technology relies on a magnetic field and radio wave pulses to generate images of the tissues and structure of a body, allowing quantitative observation of a set of features that are the subject of intervention by the magnetic resonance technology. Magnetic resonance fingerprinting (MRF) is a new method in MRI, which enables early, routine screening of certain specific cancers, multiple sclerosis, heart disease and other diseases. Each bodily tissue and disease has a unique fingerprint, which can be used to diagnose problems quickly. Through the use of a random scan sequence, MRF technology can be used to scan multiple tissues with different physical characteristics simultaneously, to generate a magnetic resonance image comprising brightness curves for multiple tissues. Thus, a physician can use the magnetic resonance image that includes brightness curves for multiple tissues to diagnose diseases.

Theoretically, when the respective trends of the multiple brightness curves in a magnetic resonance image differ significantly, the physician can accurately distinguish the characteristics of multiple tissues in one image, and can therefore observe, compare and analyze the multiple tissues in the image simultaneously. Conversely, when the respective trends of the multiple brightness curves in a magnetic resonance image are close to each other, it is not possible to isolate the characteristics of the multiple tissues from the image, in which case the magnetic resonance image cannot assist the physician in diagnosing diseases. However, if different random scan sequences are used for different tissues, the differences between the trends of multiple brightness curves of tissues in one magnetic resonance image generated by an MRF method are also different. At present, it is still not possible to find out in advance which random scan sequence should be used for certain tissues in order to generate a magnetic resonance image comprising brightness curves corresponding to these tissues with significantly different trends. It is necessary to use multiple different random sequences for multiple tissues, to generate multiple magnetic resonance images, and then to select from amongst the multiple magnetic resonance images thus generated the image in which the trends of the brightness curves corresponding to the multiple tissues differ significantly. Thus, large amounts of processing resources are wasted.

SUMMARY OF THE INVENTION

In view of the above, the present invention proposes a method for indicating tissue differentiation, for indicating the differentiation among multiple brightness curves corresponding to multiple tissues, respectively, in a magnetic resonance image generated using a random scan sequence.

A method for indicating differentiation between tissues, includes:

for each tissue amongst multiple tissues, generating a magnetization vector corresponding to each tissue on the basis of a random scan sequence;

on the basis of the magnetization vector corresponding to each of the multiple tissues, calculating a differentiation-indicating value between each pair of the multiple tissues.

The tissues are then displayed with said differentiation-indicating parameter allowing a visual differentiation in appearance between those tissues.

Preferably, the step of generating, for each tissue amongst multiple tissues, a magnetization vector corresponding to the tissue on the basis of a random scan sequence, comprises:

generating a radio frequency (RF) pulse rotation matrix $R_{RF}$ of each tissue on the basis of the random scan sequence;

generating a relaxation matrix $R_{relax}$ of each tissue on the basis of the random scan sequence;

determining whether the multiple tissues include a tissue having an off-resonance property df(Hz).

if so, then generating an off-resonance rotation matrix $R_{off}$ of each tissue having an off-resonance property on the basis of the random scan sequence, applying the RF pulse rotation matrix $R_{RF}$, the relaxation matrix $R_{relax}$ and the off-resonance rotation matrix $R_{off}$ to an initial magnetization vector, and generating a magnetization vector of each tissue by iterative calculation;

otherwise, applying the RF pulse rotation matrix $R_{RF}$ and the relaxation matrix $R_{relax}$ to an initial magnetization vector, and generating the magnetization vector of each tissue by iterative calculation.

Preferably, the random scan sequence includes at least one of the following random scan sequences: a flip angle random scan sequence and a repetition time random scan sequence.

Preferably, the step of generating an RF pulse rotation matrix $R_{RF}$ of the tissue on the basis of the random scan sequence includes:

determining whether the random scan sequence comprises the flip angle random scan sequence;

if the random scan sequence comprises the flip angle random scan sequence, generating the RF pulse rotation matrix $R_{RF}$ of each tissue on the basis of the flip angle random scan sequence;

if the random scan sequence does not comprise a flip angle random scan sequence, generating the RF pulse rotation matrix $R_{RF}$ of each tissue on the basis of a preset flip angle non-random scan sequence.

Preferably, the step of generating a relaxation matrix $R_{relax}$ of the tissue on the basis of the random scan sequence comprises:

determining whether the random scan sequence comprises a repetition time random scan sequence;

if the random scan sequence comprises a repetition time random scan sequence, generating a relaxation matrix $R_{relax}$ of each tissue on the basis of the repetition time random scan sequence;

if the random scan sequence does not include a repetition time random scan sequence, generating a relaxation matrix $R_{relax}$ of each tissue on the basis of a preset repetition time non-random scan sequence.

Preferably, the step of generating an off-resonance rotation matrix $R_{off}$ of each tissue having an off-resonance property on the basis of the random scan sequence comprises:

if the random scan sequence comprises the repetition time random scan sequence, then obtaining an off-resonance rotation matrix $R_{off}$ of each tissue having an off-resonance property on the basis of the off-resonance property df(Hz) of each tissue having an off-resonance property and the repetition time random scan sequence;

if the random scan sequence does not include the repetition time random scan sequence, then obtaining an off-resonance rotation matrix $R_{off}$ of each tissue having an off-resonance property on the basis of the off-resonance property df(Hz) of each tissue having an off-resonance property and the preset repetition time non-random scan sequence.

Preferably, the step of calculating differentiation-indicating values of the multiple tissues on the basis of the magnetization vector corresponding to each of the multiple tissues includes:

on the basis of the magnetization vector corresponding to each tissue, obtaining a tissue magnetic resonance fingerprinting (MRF) evolution vector of the tissue, each tissue MRF evolution vector comprising the modulus of a vector of projection on the XOY plane of each element in the magnetization vector corresponding to each tissue;

subjecting the tissue MRF evolution vectors of any two of the multiple tissues to cross-correlation calculation, to obtain a differentiation-indicating value of any two tissues.

Preferably, the method further includes:

on the basis of the differentiation-indicating values of the multiple tissues, generating a differentiation-indicating matrix of multiple tissues, the element in row i and column j of the differentiation-indicating matrix of multiple tissues being the differentiation-indicating value of the $i^{th}$ tissue and the $j^{th}$ tissue.

Preferably, the method further comprises determining, on the basis of the differentiation-indicating values, the differentiation between each pair of brightness curves corresponding to the multiple tissues in a magnetic resonance image generated using the random scan sequence.

Preferably, the step of determining, on the basis of the differentiation-indicating values, the differentiation between each pair of brightness curves corresponding to the multiple tissues in a magnetic resonance image generated using the random scan sequence, includes:

determining whether the differentiation-indicating value of any two of the multiple tissues is less than a set threshold;

if the differentiation-indicating value of the any two tissues is less than the set threshold, then determining that in one image, the differentiation of the two brightness curves corresponding to the any two tissues is high.

A device for indicating differentiation between tissues, includes:

a magnetization vector generating module, for generating, for each tissue among multiple tissues, a magnetization vector corresponding to each tissue on the basis of a random scan sequence;

a tissue differentiation indication acquiring module, for calculating, on the basis of the magnetization vector corresponding to each of the multiple tissues, a differentiation-indicating value between each pair of the multiple tissues.

A display displays the multiple tissues dependent on the differentiating-indicating parameter so as to present a visual difference in appearance between those tissues.

Preferably, the magnetization vector generating module includes a first rotation matrix generating sub-module, a second rotation matrix generating sub-module, a third rotation matrix generating sub-module, a determination sub-module and a magnetization vector generating sub-module:

the first rotation matrix generating sub-module is for generating an RF pulse rotation $R_{RF}$ of each tissue on the basis of the random scan sequence;

the second rotation matrix generating sub-module is for generating a relaxation matrix $R_{relax}$ of each tissue on the basis of the random scan sequence;

the determination sub-module is for determining whether the multiple tissues include a tissue having an off-resonance property df(Hz).

the third rotation matrix generating sub-module is for generating an off-resonance rotation matrix $R_{off}$ of each tissue having an off-resonance property on the basis of the random scan sequence;

the magnetization vector generating sub-module is for applying the RF pulse rotation matrix $R_{RF}$, the relaxation matrix $R_{relax}$ and the off-resonance rotation matrix $R_{off}$ to an initial magnetization vector, and generating a magnetization vector of each tissue by iterative calculation, if the determination sub-module determines that the multiple tissues include a tissue having an off-resonance property df(Hz); otherwise, for applying the RF pulse rotation matrix $R_{RF}$ and the relaxation matrix $R_{relax}$ to an initial magnetization vector, and generating the magnetization vector of each tissue by iterative calculation.

Preferably, the random scan sequence includes at least one of the following random scan sequences: a flip angle random scan sequence and a repetition time random scan sequence.

Preferably, the determination sub-module is further used for determining whether the random scan sequence comprises a flip angle random scan sequence;

the first rotation matrix generating sub-module is for generating, if the determination sub-module determines that the random scan sequence comprises a flip angle random scan sequence, the RF pulse rotation matrix $R_{RF}$ of each tissue on the basis of the flip angle random scan sequence; and if the determination sub-module determines that the random scan sequence does not comprise a flip angle random scan sequence, for generating the RF pulse rotation matrix $R_{RF}$ of each tissue on the basis of a preset flip angle non-random scan sequence.

Preferably, the determination sub-module is further used for determining whether the random scan sequence comprises a repetition time random scan sequence;

the second rotation matrix generating sub-module is for generating, if the determination sub-module determines that the random scan sequence comprises the repetition time random scan sequence, a relaxation matrix $R_{relax}$ of each tissue on the basis of the repetition time random scan sequence; and if the determination sub-module determines that the random scan sequence does not comprise a repetition time random scan sequence, for generating a relaxation matrix $R_{relax}$ of each tissue on the basis of a preset repetition time non-random scan sequence.

Preferably, the third rotation matrix generating sub-module is for obtaining an off-resonance rotation matrix $R_{off}$ of each tissue having an off-resonance property on the basis of the off-resonance property df(Hz) of each tissue having an off-resonance property and the repetition time random scan sequence, if the determination sub-module determines that the random scan sequence comprises the repetition time random scan sequence; and if the determination sub-module determines that the random scan sequence does not comprise the repetition time random scan sequence, for obtaining an off-resonance rotation matrix $R_{off}$ of each tissue having an off-resonance property on the basis of the off-resonance property df(Hz) of each tissue having an off-resonance property and the preset repetition time non-random scan sequence.

Preferably, the tissue differentiation indication acquiring module includes: a tissue MRF evolution vector calculating sub-module and a correlation calculation sub-module; wherein the tissue MRF evolution vector calculating sub-module is for obtaining, on the basis of the magnetization vector corresponding to each tissue, a tissue MRF evolution vector of each tissue, the tissue MRF evolution vector comprising the modulus of a vector of projection on the XOY plane of each element in the magnetization vector corresponding to the tissue;

the correlation calculation sub-module is for subjecting the tissue MRF evolution vectors of any two of the multiple tissues to cross-correlation calculation, to obtain a differentiation-indicating value of any two tissues.

Preferably, the tissue differentiation indication acquiring module is further used for generating, on the basis of the differentiation-indicating values of the multiple tissues, a differentiation-indicating matrix of multiple tissues, the element in row i and column j of the differentiation-indicating matrix of multiple tissues being the differentiation-indicating value of the $i^{th}$ tissue and the $j^{th}$ tissue.

Preferably, the device further includes a tissue differentiation determining module, for determining, on the basis of the differentiation-indicating values, the differentiation between each pair of brightness curves corresponding to the multiple tissues in a magnetic resonance image generated using the random scan sequence.

Preferably, the tissue differentiation determining module is for determining whether the differentiation-indicating value between any two of the multiple tissues is less than a set threshold; and if the differentiation-indicating value of the any two tissues is less than the set threshold, for determining that in one image, the differentiation of the two brightness curves corresponding to the any two tissues is high.

It can be seen from the above solution that for each tissue amongst multiple tissues a magnetization vector corresponding to the tissue is generated on the basis of a random scan sequence; a differentiation-indicating value between each pair of the multiple tissues is calculated on the basis of the magnetization vector corresponding to each of the multiple tissues. Thus, a physician can select a suitable random scan sequence, according to the method provided in the present invention, and generate a magnetic resonance image comprising multiple brightness curves corresponding to multiple tissues, such that the trends of the brightness curves corresponding to the multiple tissues in the magnetic resonance image differ significantly. Thus, the physician can then accurately distinguish the characteristics of multiple tissues in one image, and observe, compare and analyse multiple tissues in the image simultaneously.

BRIEF DESCRIPTION OF THE DRAWINGS

FIG. 5 is a magnetic resonance image of multiple tissues, provided according to an embodiment of the present invention.

FIG. 6 is a structural schematic diagram of a device for indicating differentiation between tissues, provided according to an embodiment of the present invention.

FIG. 7 is a structural schematic diagram of a magnetization vector generating module, provided according to an embodiment of the present invention.

DESCRIPTION OF THE PREFERRED EMBODIMENTS

The present invention is described in further detail below with reference to embodiments, to explain the object, technical solution and advantages thereof.

Figure 1:
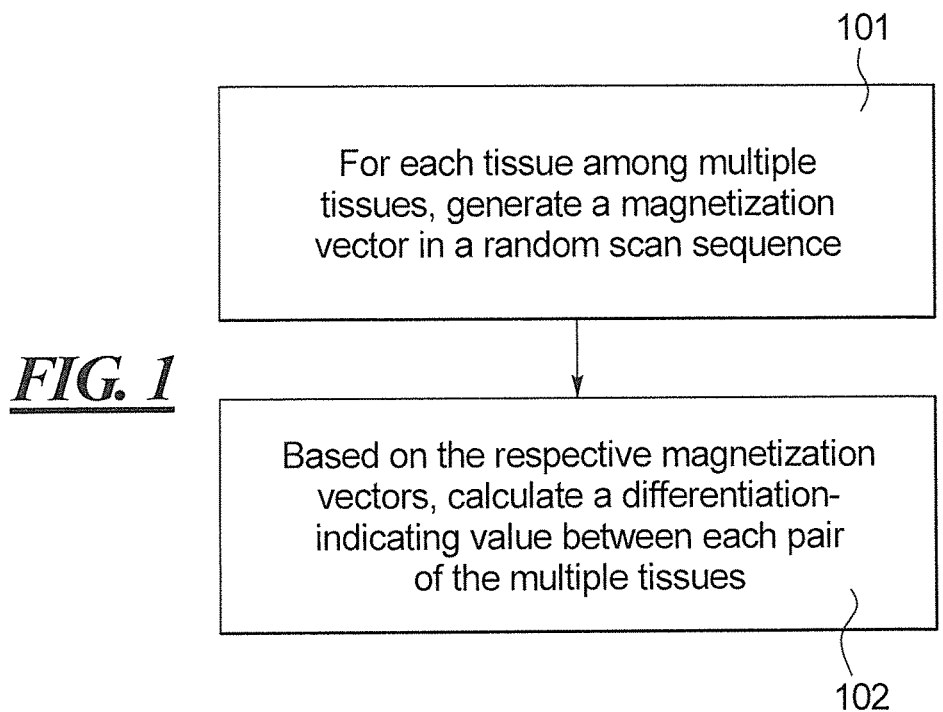
FIG. 1 is a flow chart of a method for indicating differentiation between tissues, provided according to an embodiment of the present invention.

FIG. 1 shows a method for indicating tissue differentiation provided in an embodiment of the present invention. The method may be executed by a computing device. The computing device may be a server or a PC, etc. The process of the method is described in detail below:

Step 101: for each tissue among multiple tissues, generating a magnetization vector corresponding to each tissue, on the basis of a random scan sequence.

On the basis of the random scan sequence, an RF pulse rotation matrix $R_{RF}$ of each tissue is generated. On the basis of the random scan sequence, a relaxation matrix $R_{relax}$ of each tissue is generated. A judgment is made on whether the multiple tissues include a tissue having an off-resonance property df(Hz). If they do, then on the basis of the random scan sequence, an off-resonance rotation matrix $R_{off}$ of each tissue having the off-resonance property is generated, the RF pulse rotation matrix $R_{RF}$, the relaxation matrix $R_{relax}$ and the off-resonance rotation matrix $R_{off}$ are applied to the initial magnetization vector, and a magnetization vector of each tissue is generated by iterative calculation. Otherwise, the RF pulse rotation matrix $R_{RF}$ and the relaxation matrix $R_{relax}$ are applied to the initial magnetization vector, and the magnetization vector of each tissue is generated by iterative calculation.

In one embodiment, the random scan sequence may include at least one of a flip angle random scan sequence and a repetition time random scan sequence.

Included is a step of determining whether the random scan sequence comprises the flip angle random scan sequence; if the random scan sequence comprises the flip angle random scan sequence, the RF pulse rotation matrix $R_{RF}$ of each tissue is generated on the basis of the flip angle random scan sequence; if the random scan sequence does not comprise a flip angle random scan sequence, the RF pulse rotation matrix $R_{RF}$ of each tissue is generated on the basis of a preset flip angle non-random scan sequence.

Included is a step of determining whether the random scan sequence comprises a repetition time random scan sequence; if the random scan sequence comprises a repetition time random scan sequence, a relaxation matrix $R_{relax}$ of each tissue is generated on the basis of the repetition time random scan sequence; if the random scan sequence does not comprise a repetition time random scan sequence, a relaxation matrix $R_{relax}$ of each tissue is generated on the basis of a preset repetition time non-random scan sequence.

If the random scan sequence includes the repetition time random scan sequence, an off-resonance rotation matrix $R_{off}$ of each tissue having an off-resonance property is obtained on the basis of an off-resonance property df(Hz) of each tissue having an off-resonance property and the repetition time random scan sequence; if the random scan sequence does not comprise the repetition time random scan sequence, an off-resonance rotation matrix $R_{off}$ on of each tissue having an off-resonance property is obtained on the basis of an off-resonance property df(Hz) of each tissue having an off-resonance property and the preset repetition time non-random scan sequence.

Step 102: on the basis of the magnetization vector corresponding to each of the multiple tissues, calculating a differentiation-indicating value between each pair of the multiple tissues.

For each of the multiple tissues, a tissue MRF evolution vector of the tissue may be obtained on the basis of the magnetization vector corresponding to the tissue, the tissue MRF evolution vector comprising the modulus of a vector of projection on the XOY plane of each element in the magnetization vector corresponding to the tissue; the tissue MRF evolution vectors of any two of the multiple tissues can then be subjected to cross-correlation calculation, to obtain a differentiation-indicating value for any two tissues.

Further, a differentiation-indicating matrix of multiple tissues may be generated on the basis of the differentiation-indicating values of the multiple tissues; the element in row i and column j of the differentiation-indicating matrix of the multiple tissues is the differentiation-indicating value for the $i^{th}$ tissue and the $j^{th}$ tissue.

Further, on the basis of the differentiation-indicating values, the differentiation between each pair of brightness curves corresponding to the multiple tissues, respectively, in a magnetic resonance image generated using the random scan sequence is determined.

Specifically, a judgment can be made on whether the differentiation-indicating values of the multiple tissues are less than a set threshold; if the differentiation-indicating values of the multiple tissues are less than the preset threshold, it can be determined that in one image, the differentiation between the multiple brightness curves corresponding to the multiple tissues, respectively, is high; otherwise, it can be determined that in one image, the differentiation between the multiple brightness curves corresponding to the multiple tissues, respectively, is low.

Figure 2:
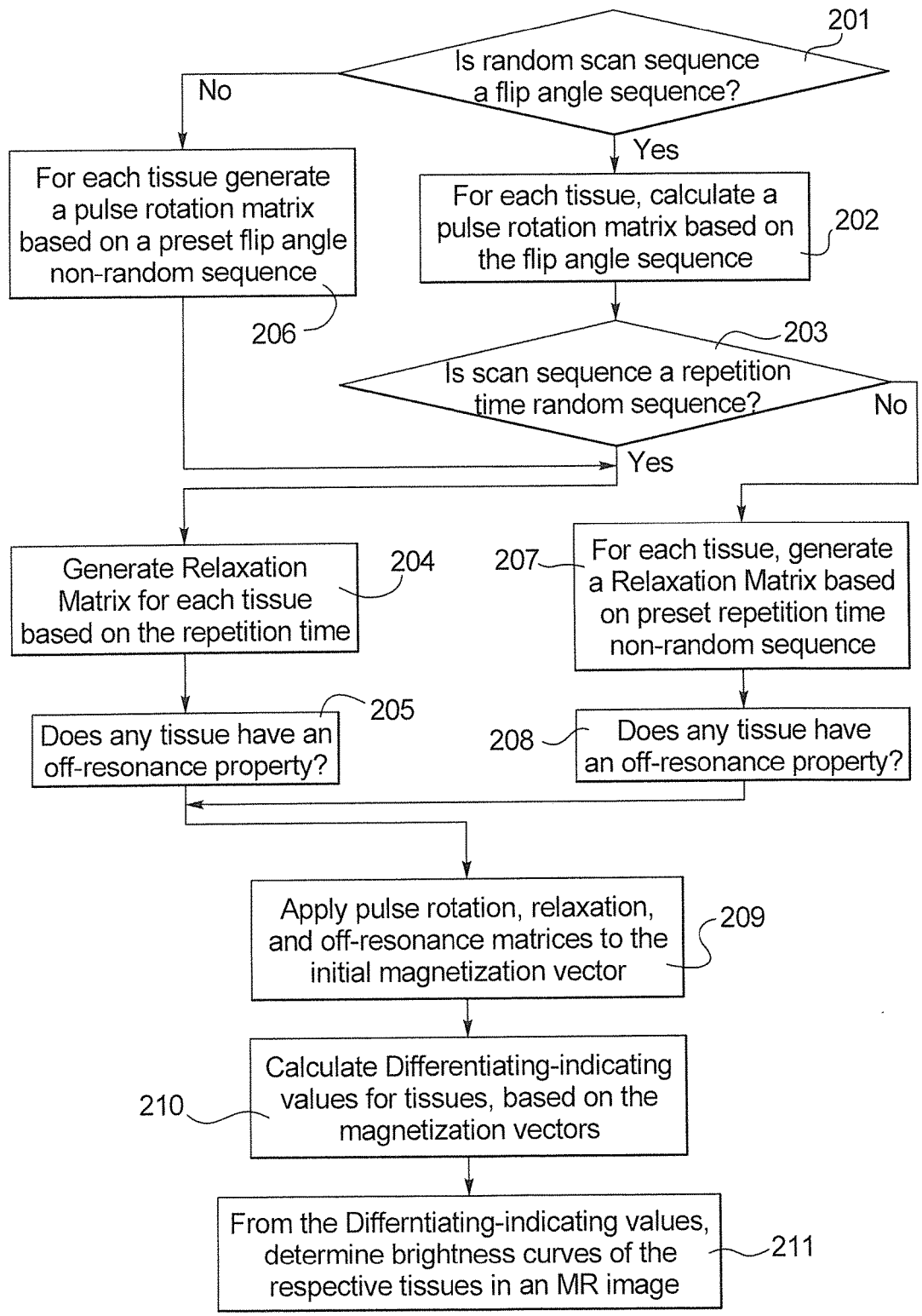
FIG. 2 is another flow chart of a method for indicating differentiation between tissues, provided according to an embodiment of the present invention.

The method in an embodiment of the present invention for indicating differentiation between tissues is described in detail below in conjunction with a specific example. FIG. 2 is another schematic flow chart of the method for indicating differentiation between tissues according to an embodiment of the present invention. The method may be executed by a computing device. The computing device may be a server or a PC, etc.

As FIG. 2 shows, the method may specifically include the following steps:

Step 201: determining whether a random scan sequence includes a flip angle random scan sequence;

the random scan sequence comprises at least one of the following random scan sequences: a flip angle random scan sequence and a repetition time random scan sequence.

If the random scan sequence comprises a flip angle random scan sequence, step 202 is executed. Otherwise, step 206 is executed.

Step 202: for each tissue among multiple tissues, an RF pulse rotation matrix $R_{RF}$ of the tissue is generated on the basis of a flip angle (FA) random scan sequence FA(i) (i=1, 2, . . . , N).

Specifically, on the basis of the flip angle random sequence, a flip angle α and a phase φ of an RF pulse are obtained. The phase φ is rotated along the z axis, to obtain a rotation matrix $Rot_Z(\phi)$. The flip angle α is rotated along the x axis, to obtain a rotation matrix $Rot_X(\alpha)$. Furthermore, −φ is rotated along the z axis, to obtain a rotation matrix $Rot_Z(-\phi)$. On the basis of $Rot_Z(\phi)$, $Rot_X(\alpha)$ and $Rot_Z(-\phi)$, an RF pulse rotation matrix $R_{RF}$ corresponding to the tissue is obtained. The RF pulse rotation matrix $R_{RF}$ is applied to the initial magnetization vector, and a magnetization vector resulting from the action of $R_{RF}$ of the tissue is generated by an iterative method.

Figure 3:
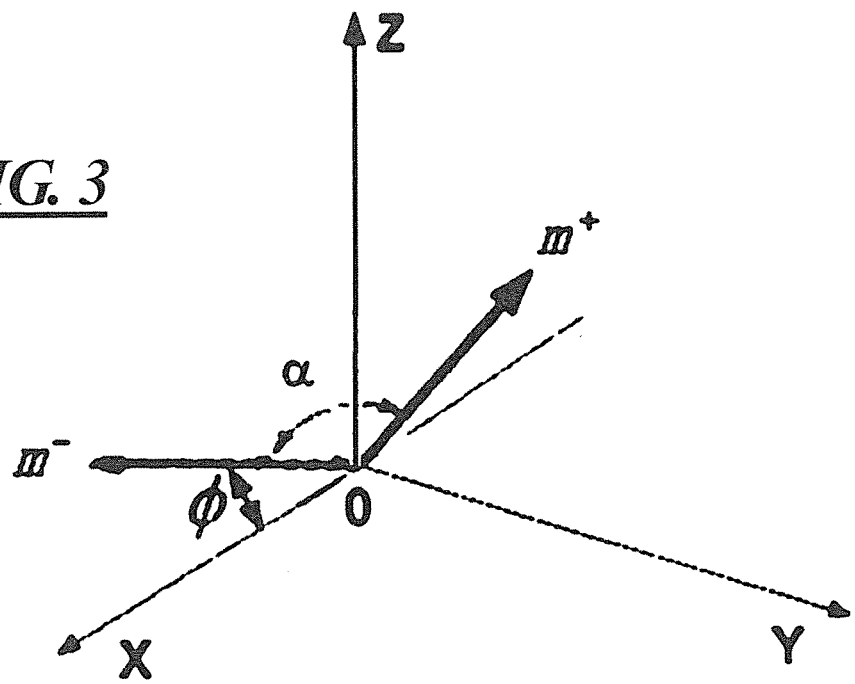
FIG. 3 is a schematic diagram showing calculation of a magnetization vector resulting from the action of an off-resonance rotation matrix, provided according to an embodiment of the present invention.

In a specific embodiment, as FIG. 3 shows, the flip angle α of the RF pulse can be obtained on the basis of the flip angle random scan sequence FA(i) by formula (1) below:

$$\alpha = abs(FA(i)), i=1,2,\ldots,N \qquad (1)$$

The phase φ can be obtained on the basis of the flip angle random scan sequence FA(i) by formula (2) below:

$$\phi = angle(FA(i)), i=1,2,\ldots,N \qquad (2)$$

The phase φ can be rotated along the z axis by means of formula (3) below, to obtain a rotation matrix $Rot_Z(\phi)$:

$$Rot_Z(\phi) = \begin{pmatrix} \cos(\phi) & \sin(\phi) & 0 \\ -\sin(\phi) & \cos(\phi) & 0 \\ 0 & 0 & 1 \end{pmatrix} \qquad (3)$$

The flip angle α of the RF pulse can be rotated along the x axis by means of formula (4) below, to obtain a rotation matrix $Rot_X(\alpha)$.

$$Rot_Y(\phi) = \begin{pmatrix} 1 & 0 & 0 \\ 0 & \cos(\alpha) & \sin(\alpha) \\ 0 & -\sin(\alpha) & \cos(\alpha) \end{pmatrix} \qquad (4)$$

−φ can be rotated along the z axis by means of formula (5) below, to obtain a rotation matrix $Rot_Z(-\phi)$:

$$Rot_Z(-\phi) = \begin{pmatrix} \cos(-\phi) & \sin(-\phi) & 0 \\ -\sin(-\phi) & \cos(-\phi) & 0 \\ 0 & 0 & 1 \end{pmatrix} \qquad (5)$$

An RF pulse rotation matrix $R_{RF}$ can be obtained on the basis of $Rot_Z(\phi)$, $Rot_X(\alpha)$ and $Rot_Z(-\phi)$, by formula (6) below:

$$R_{RF} = Rot_Z(\phi) Rot_X(\alpha) Rot_Z(-\phi) \qquad (6)$$

Figure 4:
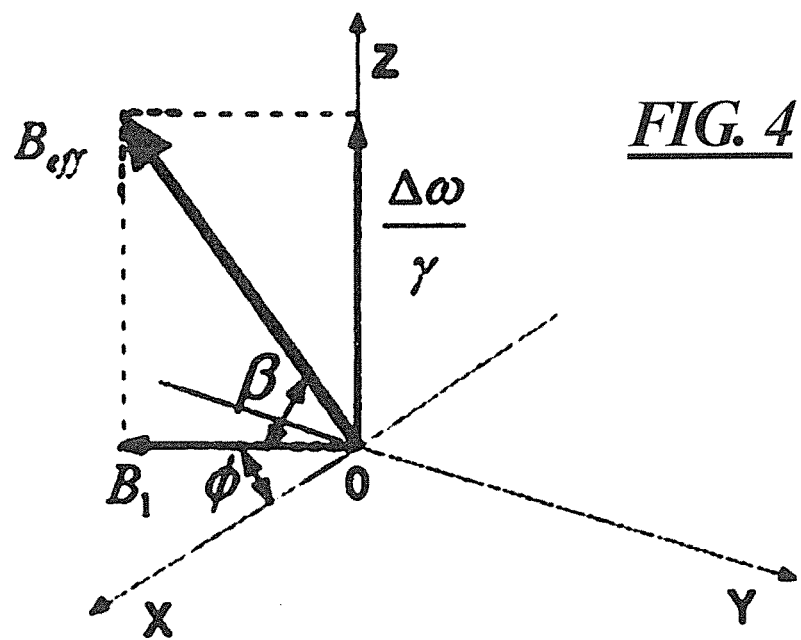
FIG. 4 is another schematic diagram showing calculation of a magnetization vector resulting from the action of an off-resonance rotation matrix, provided according to an embodiment of the present invention.

In a specific embodiment, as shown in FIG. 4, a field inhomogeneity phase β may also be used to calculate the RF pulse rotation matrix $R_{RF}$. Specifically, the effective RF pulse flip angle α' and the field inhomogeneity phase β are calculated separately on the basis of a frequency offset Δω, gyromagnetic ratio γ and RF field B1. The phase φ of the RF pulse is calculated on the basis of the flip angle random sequence. The RF field inhomogeneity phase β is rotated along the y axis, to obtain a rotation matrix $Rot_Y(\beta)$. The RF field inhomogeneity phase −β is rotated along the y axis, to obtain a rotation matrix $Rot_Y(-\beta)$. The effective RF pulse flip angle α' is rotated along the x axis, to obtain a rotation matrix $Rot_X(\alpha')$. The phase φ is rotated along the z axis, to obtain a rotation matrix $Rot_Z(-\phi)$. −φ can be rotated along the z axis by means of formula (5) above, to obtain a rotation matrix $\text{Rot}_Z(-\phi)$. An RF pulse rotation matrix $R_{RF}$ is obtained on the basis of $\text{Rot}_Z(\phi)$, $\text{Rot}_X(\alpha')$, $\text{Rot}_Z(-\phi)$, $\text{Rot}_Y(\beta)$ and $\text{Rot}_Y(-\beta)$.

In a specific embodiment, the effective RF pulse flip angle $\alpha'$ can be calculated by means of formula (7) below, on the basis of the frequency offset $\Delta\omega$, gyromagnetic ratio $\gamma$ and RF field B1:

$$\alpha' = \int_{t_0}^{t_0+\tau} \sqrt{(\Delta\omega)^2 + (\gamma B_1)^2}\, dt \tag{7}$$

The frequency offset $\Delta\omega$ at a specific spatial position $\vec{r}$ and time t can be calculated by means of formula (8) below using the magnetic field strength B, the set background field strength B0, the gyromagnetic ratio $\gamma$ and the position vector $\vec{z}$ in the z direction:

$$\Delta\omega(\vec{r},t) = \gamma(B_0 - B(\vec{r},t))\vec{z} \tag{8}$$

The phase $\phi$ may be obtained by means of formula (2) above, on the basis of the flip angle random scan sequence FA(i).

The field inhomogeneity phase $\beta$ may be calculated by means of formula (9) below:

$$\beta = \arctan\left(\frac{\Delta\omega}{\gamma B_1}\right) \tag{9}$$

The RF field inhomogeneity phase $\beta$ may be rotated along the y axis by means of formula (10) below, to obtain a rotation matrix $\text{Rot}_Y(\beta)$;

$$\text{Rot}_Y(\beta) = \begin{pmatrix} \cos(\beta) & 0 & \sin(\beta) \\ 0 & 1 & 0 \\ -\sin(\beta) & 0 & \cos(\beta) \end{pmatrix} \tag{10}$$

The RF field inhomogeneity phase $-\beta$ may be rotated along the y axis by means of formula (11) below, to obtain a rotation matrix $\text{Rot}_Y(-\beta)$;

$$\text{Rot}_Y(-\beta) = \begin{pmatrix} \cos(-\beta) & 0 & \sin(-\beta) \\ 0 & 1 & 0 \\ -\sin(-\beta) & 0 & \cos(-\beta) \end{pmatrix} \tag{11}$$

The effective RF pulse flip angle $\alpha'$ may be rotated along the x axis by means of formula (12) below, to obtain a rotation matrix $\text{Rot}_X(\alpha')$;

$$\text{Rot}_X(\alpha') = \begin{pmatrix} 1 & 0 & 0 \\ 0 & \cos(\alpha') & \sin(\alpha') \\ 0 & -\sin(\alpha') & \cos(\alpha') \end{pmatrix} \tag{12}$$

The phase $\phi$ may be rotated along the z axis by means of formula (3) above, to obtain a rotation matrix $\text{Rot}_Z(\phi)$. $-\phi$ may be rotated along the z axis by means of formula (5) above, to obtain a rotation matrix $\text{Rot}_Z(-\phi)$.

An RF pulse rotation matrix $R_{RF}$ may be obtained by means of formula (13) below, on the bases of $\text{Rot}_Z(\phi)$, $\text{Rot}_X(\alpha')$, $\text{Rot}_Z(-\phi)$, $\text{Rot}_Y(\beta)$ and $\text{Rot}_Y(-\beta)$:

$$R_{RF} = \text{Rot}_Z(\phi)\text{Rot}_Y(\beta)\text{Rot}_X(\alpha')\text{Rot}_Y(-\beta)\text{Rot}_Z(-\phi) \tag{13}$$

Step 203: determining whether the random scan sequence includes a repetition time random scan sequence.

If the random scan sequence comprises a repetition time random scan sequence, step 204 is executed. Otherwise, step 207 is executed.

Step 204: for each of the multiple tissues, a relaxation matrix $R_{relax}$ of the tissue is generated, on the basis of the repetition time (Time of Repeat, TR) random scan sequence TR(i) (i=1, 2, . . . , N).

Specifically, the relaxation matrix $R_{relax}$ of the tissue may be obtained on the basis of the repetition time random sequence, the longitudinal relaxation time constant T1 of the tissue, and the transverse relaxation time constant T2 of the tissue. By applying the relaxation matrix $R_{relax}$ of the tissue to the magnetization vector $m^-$, a magnetization vector $m^+$ resulting from the action of the relaxation matrix $R_{relax}$ of the tissue may be obtained. Here, T1 and T2 reflect the properties of the tissue.

In a specific embodiment, a relaxation matrix $R_{relax}$ may be obtained by means of formulas (14) and (15) below, on the basis of the repetition time TR:

$$\Delta t = TR(i) \quad i = 1, 2, \ldots, N \tag{14}$$

$$R_{relax} = \begin{pmatrix} e^{-\frac{\Delta t}{T_2}} & 0 & 0 \\ 0 & e^{-\frac{\Delta t}{T_2}} & 0 \\ 0 & 0 & 1 - e^{-\frac{\Delta t}{T_1}} \end{pmatrix} \tag{15}$$

where T1 is the longitudinal relaxation time constant and T2 is the transverse relaxation time constant.

Step 205: determining whether the multiple tissues include a tissue having an off-resonance property df(Hz). If the multiple tissues include a tissue having an off-resonance property df(Hz), then for each tissue having an off-resonance property df(Hz) amongst the multiple tissues, an off-resonance rotation matrix $R_{off}$ of the tissue is generated on the basis of the off-resonance property df(Hz) of the tissue and the repetition time random scan sequence.

Specifically, an off-resonance phase angle $\phi_{off}$ (units rad) may be generated on the basis of the repetition time random sequence TR(i) and the off-resonance property df(Hz) of the tissue. An off-resonance rotation matrix $R_{off}$ may be generated on the basis of the off-resonance phase angle $\phi_{off}$. A magnetization vector $m^+$ resulting from the action of $R_{off}$ may be obtained by applying the off-resonance rotation matrix $R_{off}$ to the magnetization vector $m^-$.

In a specific embodiment, the off-resonance phase angle $\phi_{off}$ may be generated by means of formula (16) below, on the basis of the repetition time random sequence TR(i) and the off-resonance property df(Hz) of the tissue:

$$\phi_{off} = df(\text{Hz}) \cdot TR(i) \cdot 2\pi \tag{16}$$

The off-resonance rotation matrix $R_{off}$ is generated by means of formula (17) below, on the basis of the off-resonance phase angle $\phi_{off}$:

$$R_{\textit{off}} = \begin{bmatrix} \cos(\varphi_{\textit{off}}/2) & \sin(\varphi_{\textit{off}}/2) & 0.0 \\ -\sin(\varphi_{\textit{off}}/2) & \cos(\varphi_{\textit{off}}/2) & 0.0 \\ 0.0 & 0.0 & 1.0 \end{bmatrix} \quad (17)$$

After step 205 is executed, a jump is made to step 209.

Step 206: for each of the multiple tissues, an RF pulse rotation matrix $R_{RF}$ of the tissue is generated on the basis of a preset flip angle non-random scan sequence;

In one embodiment, the flip angle non-random scan sequence may be a flip angle sine sequence, or a flip angle cosine sequence, etc.

The method for obtaining a magnetization vector resulting from the action of the RF pulse rotation matrix $R_{RF}$ of the tissue on the basis of the flip angle non-random scan sequence is the same as the method in step 202. The flip angle α and phase ϕ are obtained on the basis of the flip angle non-random scan sequence.

After step 206 is executed, a jump is made to step 204.

Step 207: for each of the multiple tissues, a relaxation matrix $R_{relax}$ of the tissue is generated on the basis of a preset repetition time non-random scan sequence;

In one embodiment, the repetition time non-random scan sequence may be a repetition time sine sequence, or a repetition time cosine sequence, etc.

The method for obtaining a magnetization vector resulting from the action of the relaxation matrix $R_{relax}$ of the tissue on the basis of the preset repetition time non-random scan sequence is the same as the method in step 204. The relaxation matrix $R_{relax}$ of the tissue may be obtained on the basis of the repetition time non-random sequence, the longitudinal relaxation time constant T1 of the tissue, and the transverse relaxation time constant T2 of the tissue.

Step 208: determining whether the multiple tissues include a tissue having an off-resonance property df(Hz). If the multiple tissues include a tissue having an off-resonance property df(Hz), then for each tissue having an off-resonance property df(Hz) amongst the multiple tissues, an off-resonance rotation matrix $R_{\textit{off}}$ of the tissue is generated on the basis of the off-resonance property df(Hz) of the tissue and the repetition time non-random scan sequence.

The method by which a magnetization vector resulting from the action of the off-resonance rotation matrix $R_{\textit{off}}$ of the tissue may be obtained on the basis of the off-resonance property df(Hz) of the tissue and the repetition time non-random scan sequence is the same as the method in step 205. The off-resonance phase angle $\phi_{\textit{off}}$ is generated on the basis of the repetition time random sequence TR(i) and the off-resonance property df(Hz) of the tissue.

Step 209: If it is determined that the multiple tissues include a tissue having an off-resonance property df(Hz), then the RF pulse rotation matrix $R_{RF}$, the relaxation matrix $R_{relax}$ and the off-resonance rotation matrix $R_{\textit{off}}$ are applied to the initial magnetization vector, and a magnetization vector of each tissue is generated by iterative calculation; otherwise, the RF pulse rotation matrix $R_{RF}$ and the relaxation matrix $R_{relax}$ are applied to the initial magnetization vector, and the magnetization vector of each tissue is generated by iterative calculation.

A magnetization vector $m^+$ resulting from the action of the RF pulse rotation matrix $R_{RF}$ may be calculated by means of formula (18) below, by an iterative method:

$$m^+ = R_{RF} \cdot m^- \quad (18)$$

where $m^-$ is the magnetization vector before the action of the RF pulse rotation matrix $R_{RF}$ on the occasion in question; in a specific embodiment, the initial magnetization vector may be set as $m_0 = [0,0,-1]^T$. When the field inhomogeneity phase β can also be used to calculate the RF pulse rotation matrix $R_{RF}$, the initial magnetization vector quantity may be set as the effective RF field $\vec{B}_{\textit{eff}}$. As FIG. 4 shows, the effective RF field $\vec{B}_{\textit{eff}}$ is calculated by means of formula (8) above. The effective RF field $\vec{B}_{\textit{eff}}$ may be calculated by formula (19) below:

$$\vec{B}_{\textit{eff}} = \vec{B}_1 + \left(\frac{\Delta\omega}{\gamma}\right) \cdot \vec{z} \quad (19)$$

where B1 is the RF field and $$\frac{\Delta\omega}{\gamma}$$

is the field offset.

The relaxation matrix $R_{relax}$ of the tissue may be applied to the magnetization vector $m^-$ by means of formula (20) below, to obtain a magnetization vector $m^+$ resulting from the action of the relaxation matrix $R_{relax}$ of the tissue:

$$m^+ = R_{relax} \cdot m^- \quad (20)$$

where $m^-$ is the magnetization vector before the action of $R_{relax}$; in a specific embodiment, the initial magnetization vector may be set as $m_0 = [0,0,-1]^T$.

By applying the off-resonance rotation matrix $R_{\textit{off}}$ of the tissue to the magnetization vector $m^-$ by means of formula (21) below, a magnetization vector $m^+$ resulting from the action of the off-resonance rotation matrix $R_{\textit{off}}$ of the tissue may be obtained:

$$m^+ = R_{\textit{off}} \cdot m^- \quad (21).$$

Here, $m^-$ is the magnetization vector before the action of $R_{\textit{off}}$; in a specific embodiment, the initial magnetization vector may be set as $m_0 = [0,0,-1]^T$).

Step 210: differentiation-indicating values of the multiple tissues are calculated on the basis of the magnetization vector corresponding to each of the tissues; wherein the differentiation-indicating values of the multiple tissues can indicate the differentiation among multiple brightness curves corresponding to the multiple tissues, respectively, in one image.

In a specific embodiment, the differentiation-indicating values of multiple tissues may be obtained by the following method:

For each of the multiple tissues, a tissue MRF evolution vector of the tissue is obtained on the basis of the magnetization vector corresponding to the tissue. The tissue MRF evolution vector includes the modulus of a vector of projection on the XOY plane of each element in the magnetization vector corresponding to the tissue. The tissue MRF evolution vectors of any two of the multiple tissues are subjected to cross-correlation calculation, to obtain a differentiation-indicating value for any two tissues.

For example, the tissue MRF evolution vector of a tissue Ti may be obtained by the following method: in accordance with steps 201-203 above, N iterative operations are performed taking the initial magnetization vector as the initial value, to obtain N magnetization vectors of the tissue Ti; the vector quantities of the projection of the N magnetization vectors on the XOY plane are then used as N vector quantities of the tissue MRF evolution vector. For example, the initial magnetization vector $m_0$ may be used as the initial value, and magnetization vectors $(m_1-m_N)$ of the tissue Ti may be obtained in sequence in accordance with the iterative method in steps 201-203 above. The moduli S(1)–S(N) of the vector quantities of the projection of the magnetization vectors $(m_1-m_N)$ on the XOY plane can be calculated separately, to obtain $S_{Ti}=[|S(1)|, |S(2)|, \ldots, |S(N)|]$.

In a specific embodiment, the tissue MRF evolution vectors of tissues Ti and Tj can be subjected to cross correlation by means of formula (22) below, to obtain a differentiation-indicating value $R_{Ti,Tj}$ for tissues Ti and Tj:

$$R_{Ti,Tj} = \frac{E\{[S_{Ti} - \mu_{Ti}] \cdot [S_{Tj} - \mu_{Tj}]\}}{\sqrt{E\{|S_{Ti}|^2\} \cdot E\{|S_{Tj}|^2\}}} \quad (22)$$

where $S_{Ti}$ is the tissue vector quantity of tissue Ti; $S_{Tj}$ is the tissue vector quantity of tissue Tj; $\mu_{Ti}$ is the mean brightness value of tissue Ti; $\mu_{Tj}$ is the mean brightness value of tissue Tj.

In another specific embodiment, differentiation-indicating values for multiple tissues may also be obtained by methods such as correlation evaluation, mode identification and machine learning.

Further, a differentiation-indicating matrix of multiple tissues may also be generated on the basis of the differentiation-indicating values of the multiple tissues. The element in row i and column j of the differentiation-indicating matrix of the multiple tissues is the differentiation-indicating value for the $i^{th}$ tissue and the $j^{th}$ tissue. Specifically, the matrix may be expressed as:

$$\begin{array}{cccc} Tis1 & Tis2 & \ldots & TisM \end{array}$$
$$\begin{bmatrix} 1.0 & C_{12} & \ldots & C_{1M} \\ C_{21} & 1.0 & \ldots & C_{2M} \\ \vdots & \vdots & \ddots & \vdots \\ C_{M1} & C_{M2} & \ldots & 1.0 \end{bmatrix} \begin{array}{c} Tis1 \\ Tis2 \\ \vdots \\ TisM \end{array}$$

wherein the matrix has M columns and M rows, representing M tissues, respectively. The element $C_{ij}$ in row i and column j of the matrix is the differentiation-indicating value for the two tissues Ti and Tj.

Step 211: on the basis of the differentiation-indicating values of the multiple tissues, determining the differentiation among brightness curves corresponding to the multiple tissues in a magnetic resonance image generated using the random scan sequence.

Specifically, a judgment can be made on whether the differentiation-indicating values obtained for the multiple tissues are less than a set threshold. If the differentiation-indicating values of the multiple tissues are less than the preset threshold, then in one image, the differentiation between the multiple brightness curves corresponding to the multiple tissues, respectively, is high.

In a specific embodiment, the differentiation-indicating value of any two of the multiple tissues can be obtained from the matrix. If the differentiation-indicating values obtained for any two tissues are all less than a set threshold, then an image exhibiting a high level of differentiation among the multiple tissues can be obtained using the flip angle random scan sequence and the repetition time random scan sequence, i.e. in one image, the trends of the multiple brightness curves corresponding to the multiple tissues, respectively, differ significantly.

In another specific embodiment, the differentiation-indicating values of any two of the multiple tissues are obtained separately. The indicating values may be obtained by means of a negation operation in which the tissue MRF evolution vectors of two tissues undergo cross correlation. If the differentiation-indicating values obtained for any two tissues are all greater than a set threshold, then an image exhibiting a high level of differentiation among the multiple tissues can be obtained using the flip angle random scan sequence and the repetition time random scan sequence, i.e. in one image, the trends of the multiple brightness curves corresponding to the multiple tissues, respectively, differ significantly.

By way of demonstration, when the flip angle random scan sequence is $$FA_t = 10 + \sin\left(\frac{2\pi}{500} \cdot t\right) \times 50 + random(5)$$

and the repetition time random scan sequence is $TR_t=U(4)+10.0$, the differentiation among brightness curves corresponding to multiple tissues (CSF, fat, white matter, gray matter, white matter –30 Hz) in a magnetic resonance image generated using these random scan sequences may be determined by the method described above. White matter –30 Hz means white matter with a –30 Hz off-resonance property. The characteristic parameters for each tissue are shown in the table below:

TABLE 1

Characteristic parameters of tissues

| Tissue | T1 (ms) | T2 (ms) | Off-resonance property (Hz) |
|---|---|---|---|
| CSF | 4880 | 550 | 0 |
| Fat | 240 | 84 | 0 |
| White matter | 685 | 65 | 0 |
| Gray matter | 1180 | 97 | 0 |
| White matter –30 Hz | 685 | 65 | –30 |

The following table shows differentiation-indicating values obtained by the method shown in FIG. 2 for any two tissues:

TABLE 2

Differentiation-indicating values of tissues

| Differentiation-indicating values of tissues | CSF | Fat | White matter | Gray matter | WM (–30 Hz) |
|---|---|---|---|---|---|
| CSF | 1.0 | … | … | … | … |
| Fat | 0.4579 | 1.0 | … | … | … |
| White matter | 0.5886 | 0.9226 | 1.0 | … | … |
| Gray matter | 0.7159 | 0.8318 | 0.9657 | 1.0 | … |
| WM (–30 Hz) | 0.4293 | 0.7257 | 0.8331 | 0.7812 | 1.0 |

As table 2 shows, the intersection of any two tissues shows the differentiation-indicating value for these two tissues. For example, the differentiation-indicating value for white matter and fat is 0.9226, while the differentiation-indicating value for CSF and fat is 0.4579.

According to the differentiation-indicating values of tissues shown in table 2, if the threshold is set as 0.7, then since the differentiation-indicating value for CSF and fat and the differentiation-indicating value for WM (−30 Hz) and CSF are all less than the set threshold, the differentiation among the multiple brightness curves corresponding to white matter, fat, CSF and WM (−30 Hz), respectively, in one image will be high.

FIG. 5 is a magnetic resonance image generated using the flip angle random scan sequence and repetition time random scan sequence in this embodiment. The image has brightness curves corresponding to CSF, fat, white matter, gray matter and WM (−30 Hz), respectively. It can be seen from FIG. 5 that the trends of brightness curves corresponding to tissues for which the tissue differentiation-indicating value is less than the set threshold differ to a greater extent, for example CSF and fat. The trends of brightness curves corresponding to tissues for which the tissue differentiation-indicating value is greater than the set threshold differ to a lesser extent, for example white matter and fat.

It can be seen from the above solution that in the present invention, for each tissue amongst multiple tissues a magnetization vector corresponding to each tissue is generated on the basis of a random scan sequence; a differentiation-indicating value between each pair of the multiple tissues is calculated on the basis of the magnetization vector corresponding to each of the multiple tissues. Thus, a physician can select a suitable random scan sequence, according to the method provided in the present invention, and generate a magnetic resonance image comprising multiple brightness curves corresponding to multiple tissues, such that the trends of the brightness curves corresponding to the multiple tissues in the magnetic resonance image differ significantly. Thus, the physician can then accurately distinguish the characteristics of multiple tissues in one image, and observe, compare and analyse multiple tissues in the image simultaneously.

The embodiments of the present invention also propose a device for indicating tissue differentiation. FIG. 6 is a structural schematic diagram of a device for indicating tissue differentiation provided according to an embodiment of the present invention. As FIG. 6 shows, the device has a magnetization vector generating module 301 and a tissue differentiation indication acquiring module 302.

The magnetization vector generating module 301 is for generating, for each tissue amongst multiple tissues, a magnetization vector corresponding to each tissue on the basis of a random scan sequence;

The tissue differentiation indication acquiring module 302 is for calculating a differentiation-indicating value between each pair of the multiple tissues, on the basis of the magnetization vector corresponding to each of the multiple tissues.

The random scan sequence comprises at least one of the following random scan sequences: a flip angle random scan sequence and a repetition time random scan sequence.

Specifically, as FIG. 7 shows, the magnetization vector generating module comprises a first rotation matrix generating sub-module 3011, a second rotation matrix generating sub-module 3012, a third rotation matrix generating sub-module 3013, a determination sub-module 3014, and a magnetization vector generating sub-module 3015.

The first rotation matrix generating sub-module 3011 is for generating an RF pulse rotation matrix $R_{RF}$ of each tissue on the basis of the random scan sequence. The second rotation matrix generating sub-module 3012 is for generating a relaxation matrix $R_{relax}$ of each tissue on the basis of the random scan sequence. The determination sub-module 3014 is for determining whether the multiple tissues include a tissue having an off-resonance property df(Hz). The third rotation matrix generating sub-module 3013 is for generating an off-resonance rotation matrix $R_{off}$ of each tissue having an off-resonance property on the basis of the random scan sequence. The magnetization vector generating sub-module 3015 is for applying the RF pulse rotation matrix $R_{RF}$, the relaxation matrix $R_{relax}$ and the off-resonance rotation matrix $R_{off}$ to an initial magnetization vector if the determination sub-module 3014 determines that the multiple tissues include a tissue having an off-resonance property df(Hz), and generating a magnetization vector of each tissue by iterative calculation; otherwise, for applying the RF pulse rotation matrix $R_{RF}$ and the relaxation matrix $R_{relax}$ to an initial magnetization vector, and generating the magnetization vector of each tissue by iterative calculation.

The determination sub-module 3014 is further used for determining whether the random scan sequence comprises a flip angle random scan sequence. The first rotation matrix generating sub-module 3011 is for generating the RF pulse rotation matrix $R_{RF}$ of each tissue on the basis of the flip angle random scan sequence if the determination sub-module 3014 determines that the random scan sequence comprises a flip angle random scan sequence; and for generating the RF pulse rotation matrix $R_{RF}$ of each tissue on the basis of a preset flip angle non-random scan sequence if the determination sub-module 3014 determines that the random scan sequence does not include a flip angle random scan sequence.

The determination sub-module 3014 is further used for determining whether the random scan sequence comprises a repetition time random scan sequence. The second rotation matrix generating sub-module 3012 is for generating a relaxation matrix $R_{relax}$ of each tissue on the basis of the repetition time random scan sequence if the determination sub-module 3014 determines that the random scan sequence comprises the repetition time random scan sequence; and for generating a relaxation matrix $R_{relax}$ of each tissue on the basis of a preset repetition time non-random scan sequence if the determination sub-module 3014 determines that the random scan sequence does not comprise a repetition time random scan sequence.

The third rotation matrix generating sub-module 3013 is for obtaining an off-resonance rotation matrix $R_{off}$ of each tissue having an off-resonance property on the basis of the off-resonance property df(Hz) of each tissue having an off-resonance property and the repetition time random scan sequence, if the determination sub-module 3014 determines that the random scan sequence comprises the repetition time random scan sequence; and for obtaining an off-resonance rotation matrix $R_{off}$ of each tissue having an off-resonance property on the basis of the off-resonance property df(Hz) of each tissue having an off-resonance property and the preset repetition time non-random scan sequence, if the determination sub-module 3014 determines that the random scan sequence does not comprise the repetition time random scan sequence.

Here, the method used by the magnetization vector generating module 301 is the same as the method in steps 201-209, and is not repeated here.

Figure 8:
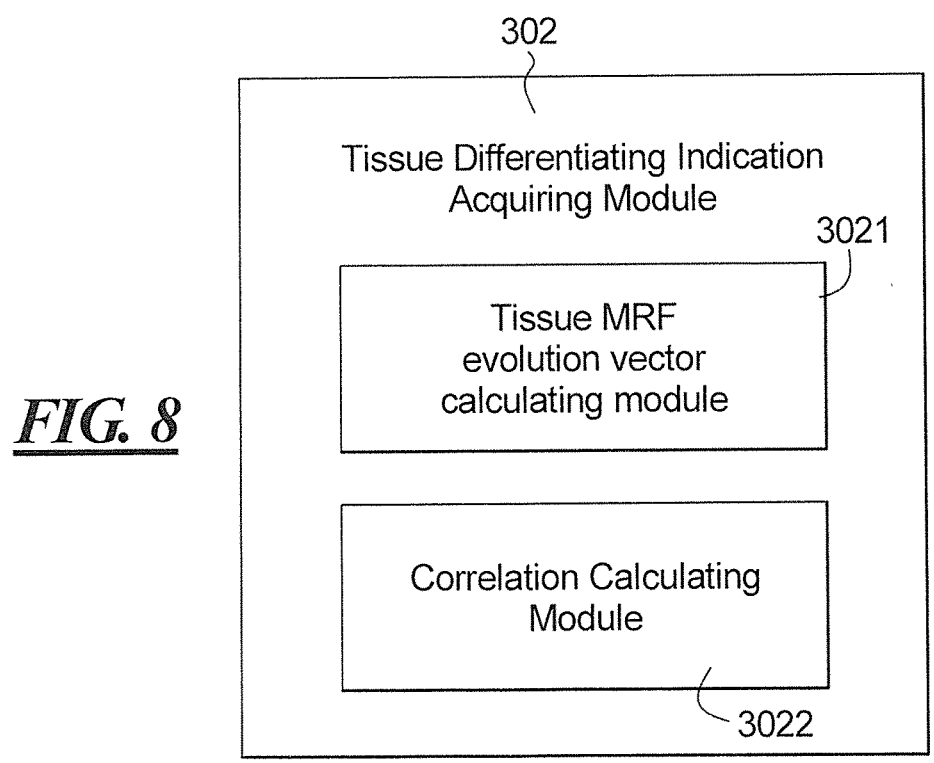
FIG. 8 is a structural schematic diagram of a tissue differentiation indication acquiring module provided according to an embodiment of the present invention.

Specifically, as FIG. 8 shows, the tissue differentiation indication acquiring module 302 includes: a tissue MRF evolution vector calculating sub-module 3021 and a correlation calculating sub-module 3022. The tissue MRF evolution vector calculating sub-module 3021 is for obtaining, for each of the multiple tissues, a tissue MRF evolution vector of the tissue on the basis of the magnetization vector corresponding to the tissue, the tissue MRF evolution vector comprising the modulus of a vector of projection on the XOY plane of each element in the magnetization vector corresponding to the tissue. The correlation calculating sub-module 3022 is for subjecting the tissue MRF evolution vector of any two of the multiple tissues to cross-correlation calculation, to obtain a differentiation-indicating value of any two tissues.

The tissue differentiation indication acquiring module 302 is further used for generating a differentiation-indicating matrix of multiple tissues on the basis of the differentiation-indicating values of the multiple tissues, with the element in row i and column j of the differentiation-indicating matrix of the multiple tissues being the differentiation-indicating value for the $i^{th}$ tissue and the $j^{th}$ tissue.

Here, the method used by the tissue differentiation indication acquiring module 302 is the same as the method in step 210, and is not repeated here.

The device further comprises a tissue differentiation determining module, for determining, on the basis of the differentiation-indicating values, the differentiation between each pair of the brightness curves corresponding to the multiple tissues in a magnetic resonance image generated using the random scan sequence.

Specifically, the tissue differentiation determining module is for determining whether the differentiation-indicating values of the multiple tissues are less than a set threshold; and if the differentiation-indicating values of the multiple tissues are less than the set threshold, determining that the differentiation among multiple brightness curves corresponding to the multiple tissues, respectively, in one image is high.

Here, the method used by the tissue differentiation determining module is the same as the method in step 211, and is not repeated here.

It can be seen from the above device that for each tissue amongst multiple tissues a magnetization vector corresponding to the tissue is generated on the basis of a random scan sequence; a differentiation-indicating value between each pair of the multiple tissues is calculated on the basis of the magnetization vector corresponding to each of the multiple tissues. Thus, a physician can select a suitable random scan sequence, according to the device provided in the present invention, and generate a magnetic resonance image including multiple brightness curves corresponding to multiple tissues, such that the trends of the brightness curves corresponding to the multiple tissues in the magnetic resonance image differ significantly. Thus, the physician can then accurately distinguish the characteristics of multiple tissues in one image, and observe, compare and analyze multiple tissues in the image simultaneously.

The present invention also provides a machine-readable storage medium which stores commands for making a machine execute the method for indicating differentiation between tissues described herein. Specifically, a system or apparatus equipped with a storage medium may be provided, wherein software program code realizing the functions of any one of the above embodiments is stored on the storage medium, and a computer (or CPU or MPU) of the system or apparatus reads and executes the program code stored on the storage medium.

In this case, the program code read from the storage medium is itself capable of realizing the functions of any one of the above embodiments, hence the program code and the storage medium on which the program code is stored form part of the present invention.

Examples of storage media used to provide program code include floppy disks, hard disks, magneto-optical disks, optical disks (eg. CD-ROM, CD-R, CD-RW, DVD-ROM, DVD-RAM, DVD-RW, DVD+RW), magnetic tape, non-volatile memory cards and ROM. Optionally, program code may be downloaded via a communication network from a server computer.

In addition, it should be clear that not only can part or all of an actual operation be completed by executing program code read out by a computer, but an operating system operating on a computer can also be made to complete part or all of the actual operation based on the commands of the program code, so as to realize the function of any one of the above embodiments.

In addition, it can be appreciated that program code read out from the storage medium is written into a memory installed in an expansion board inserted in the computer, or written into a memory installed in an expansion unit connected to the computer, and thereafter a CPU etc. installed on the expansion board or expansion unit is made to execute part or all of an actual operation based on the commands of the program code, so as to realize the function of any one of the above embodiments.

Although modifications and changes may be apparent to those of ordinary skill in the art, it is the intention of the inventor to embody within the patent warranted hereon any changes and modifications as reasonably and properly come within the scope of the inventor's contribution to the art.

I claim as my invention:

1. A method for indicating differentiation between tissues of a subject, comprising:
   in a computer, identifying multiple tissues in a subject and, for each tissue among said multiple tissues, executing a simulation comprising a random scan sequence, wherein a magnetic resonance scan of each tissue is simulated with a selected parameter of the scan being randomly varied so as to have different parameter values and in which, as a result of the different parameter values, the respective tissue is given a magnetization vector in the simulation;
   in said computer, dependent on the respective magnetization vectors for each of the multiple tissue, calculating a differentiation-indicating value between each pair of tissues among said multiple tissues;
   in said computer, simulating a pair of brightness curves for each said pair of tissues among said multiple tissues and using the respective differentiation-indicating values to differentiate between each pair of brightness curves, and thereby obtaining a differentiation for each pair of brightness curves; and
   in said computer, based on said differentiation, selecting a magnetic resonance fingerprinting (MRF) protocol for scanning the multiple tissues, and making said MRF protocol available from the computer in electronic form with a format configured to operate a magnetic resonance imaging apparatus in order to execute the selected MRF protocol.

2. The method as claimed in claim 1, comprising, in said simulation, generating, for each tissue among said multiple tissues, said magnetization vector corresponding to the tissue based on said random scan sequence, by:
   generating a radio frequency (RF) pulse rotation matrix $R_{RF}$ of each tissue on the basis of the random scan sequence;
   generating a relaxation matrix $R_{relax}$ of each tissue on the basis of the random scan sequence;
   determining whether the multiple tissues include a tissue having an off-resonance property df (Hz);
   if so, then generating an off-resonance rotation matrix $R_{off}$ of each tissue having an off-resonance property on the basis of the random scan sequence, applying the RF pulse rotation matrix $R_{RF}$, the relaxation matrix $R_{relax}$ and the off-resonance rotation matrix $R_{off}$ to an initial magnetization vector, and generating a magnetization vector of each tissue by iterative calculation; and otherwise, applying the RF pulse rotation matrix $R_{RF}$ and the relaxation matrix $R_{relax}$ to an initial magnetization vector, and generating the magnetization vector of each tissue by iterative calculation.

3. The method as claimed in claim 2, comprising selecting the random scan sequence as at least one random scan sequence from the group consisting of a flip angle random scan sequence, and a repetition time random scan sequence.

4. The method as claimed in claim 3, comprising generating said RF pulse rotation matrix $R_{RF}$ of the tissue on the basis of the random scan sequence by:

determining whether the random scan sequence comprises the flip angle random scan sequence;

if the random scan sequence comprises the flip angle random scan sequence, generating the RF pulse rotation matrix $R_{RF}$ of each tissue on the basis of the flip angle random scan sequence; and if the random scan sequence does not comprise a flip angle random scan sequence, generating the RF pulse rotation matrix $R_{RF}$ of each tissue on the basis of a preset flip angle non-random scan sequence.

5. The method as claimed in claim 3 comprising generating a relaxation matrix $R_{relax}$ of the tissue based on the random scan sequence by:

determining whether the random scan sequence comprises a repetition time random scan sequence;

if the random scan sequence comprises a repetition time random scan sequence, generating a relaxation matrix $R_{relax}$ of each tissue on the basis of the repetition time random scan sequence; and if the random scan sequence does not comprise a repetition time random scan sequence, generating a relaxation matrix $R_{relax}$ of each tissue on the basis of a preset repetition time non-random scan sequence.

6. The method as claimed in claim 5, comprising generating an off-resonance rotation matrix $R_{off}$ of each tissue having an off-resonance property based on the random scan sequence by:

if the random scan sequence comprises the repetition time random scan sequence, then obtaining an off-resonance rotation matrix $R_{off}$ each tissue having an off-resonance property on the basis of the off-resonance property df (Hz) of each tissue having an off-resonance property and the repetition time random scan sequence; and if the random scan sequence does not comprise the repetition time random scan sequence, then obtaining an off-resonance rotation matrix $R_{off}$ of each tissue having an off-resonance property on the basis of the off-resonance property df (Hz) of each tissue having an off-resonance property and the preset repetition time non-random scan sequence.

7. The method as claimed in claim 1, comprising, in said simulation, calculating said differentiation-indicating values of the multiple tissues based on the magnetization vector corresponding to each of the multiple tissues by:

based on the magnetization vector corresponding to each tissue, obtaining a tissue magnetic resonance fingerprinting (MRF) evolution vector of the tissue, each tissue MRF evolution vector comprising the modulus of a vector of projection on the XOY plane of each element in the magnetization vector corresponding to each tissue; and subjecting the tissue MRF evolution vectors of any two of the multiple tissues to cross-correlation calculation, to obtain a differentiation-indicating value of any two tissues.

8. The method as claimed in claim 7, further comprising determining, based on the differentiation-indicating values, the differentiation between each pair of brightness curves corresponding to the multiple tissues in a magnetic resonance image generated using the random scan sequence.

9. The method as claimed in claim 8, comprising determining, based on the differentiation-indicating values, the differentiation between each pair of brightness curves corresponding to the multiple tissues in a magnetic resonance image generated using the random scan sequence, by:

determining whether the differentiation-indicating value of any two of the multiple tissues is less than a set threshold; and if the differentiation-indicating value of the any two tissues is less than the set threshold, then determining that in one image, the differentiation of the two brightness curves corresponding to the any two tissues is high.

10. The method as claimed in claim 1, further comprising:

based on the differentiation-indicating values of the multiple tissues, generating a differentiation-indicating matrix of multiple tissues, the element in row i and column j of the differentiation-indicating matrix of multiple tissues being the differentiation-indicating value of the $i^{th}$ tissue and the $j^{th}$ tissue.

11. A device for indicating differentiation between tissues of a subject, comprising:

a computer configured to identify multiple tissues in a subject and, for each tissue among said multiple tissues, executing a simulation comprising a random scan sequence, wherein a magnetic resonance scan of each tissue is simulated with a selected parameter of the scan being randomly varied so as to have different parameter values and in which, as a result of the different parameter values, the respective tissue is given a magnetization vector in the simulation;

said computer being configured to calculate dependent on the respective magnetization vectors for each of the multiple tissue, a differentiation-indicating value between each pair of tissues among said multiple tissues;

said computer being configured to simulate a pair of brightness curves for each said pair of tissues among said multiple tissues and to use the respective differentiation-indicating values to differentiate between each pair of brightness curves, and thereby obtaining a differentiation for each pair of brightness curves; and said computer being configured to select, based on said differentiation, a magnetic resonance fingerprinting (MRF) protocol for scanning the multiple tissues, and to make said MRF protocol available from the computer in electronic form with a format configured to operate a magnetic resonance imaging apparatus in order to execute the selected MRF protocol.

12. The device as claimed in claim 11, wherein the computer is configured to:

generate an RF pulse rotation matrix $R_{RF}$ of each tissue on the basis of the random scan sequence; \ generate a relaxation matrix $R_{relax}$ of each tissue on the basis of the random scan sequence;

determine whether the multiple tissues include a tissue having an off-resonance property df (Hz);

generate an off-resonance rotation matrix $R_{off}$ of each tissue having an off-resonance property on the basis of the random scan sequence; and apply the RF pulse rotation matrix $R_{RF}$, the relaxation matrix $R_{relax}$ and the off-resonance rotation matrix $R_{off}$ to an initial magnetization vector, and generate a magnetization vector of each tissue by iterative calculation, if the multiple tissues include a tissue having an off-resonance property df (Hz); otherwise, to apply the RF pulse rotation matrix $R_{RF}$ and the relaxation matrix $R_{relax}$ to an initial magnetization vector, and generate the magnetization vector of each tissue by iterative calculation.

13. The device as claimed in claim 12, wherein the random scan sequence is at least one random scan sequence selected from the group consisting of a flip angle random scan sequence and a repetition time random scan sequence.

14. The device as claimed in claim 13, wherein the computer is configured to:
determine whether the random scan sequence is a flip angle random scan sequence; and
generate, if the random scan sequence comprises a flip angle random scan sequence, the RF pulse rotation matrix $R_{RF}$ of each tissue on the basis of the flip angle random scan sequence; and if the random scan sequence does not comprise a flip angle random scan sequence, generate the RF pulse rotation matrix $R_{RF}$ of each tissue on the basis of a preset flip angle non-random scan sequence.

15. The device as claimed in claim 13, wherein the computer is configured to:
determine whether the random scan sequence comprises a repetition time random scan sequence; and
generate, if the random scan sequence comprises the repetition time random scan sequence, a relaxation matrix $R_{relax}$ of each tissue on the basis of the repetition time random scan sequence; and if the random scan sequence does not comprise a repetition time random scan sequence, generate a relaxation matrix $R_{relax}$ of each tissue on the basis of a preset repetition time non-random scan sequence.

16. The device as claimed in claim 15, wherein the computer is configured to obtain an off-resonance rotation matrix $R_{off}$ of each tissue having an off-resonance property on the basis of the off-resonance property df (Hz) of each tissue having an off-resonance property and the repetition time random scan sequence, if the random scan sequence comprises the repetition time random scan sequence; and if the random scan sequence does not comprise the repetition time random scan sequence, obtain an off-resonance rotation matrix $R_{off}$ of each tissue having an off-resonance property based on the off-resonance property df (Hz) of each tissue having an off-resonance property and the preset repetition time non-random scan sequence.

17. The device as claimed in claim 11, wherein the computer is configured to:
obtain, based on the magnetization vector corresponding to each tissue, a tissue MRF evolution vector of each tissue, the tissue MRF evolution vector comprising the modulus of a vector of projection on the XOY plane of each element in the magnetization vector corresponding to the tissue; and
subject the tissue MRF evolution vectors of any two of the multiple tissues to cross-correlation calculation, to obtain a differentiation-indicating value of any two tissues.

18. The device as claimed in claim 17, wherein the computer is further configured to determine, based on the differentiation-indicating values, the differentiation between each pair of brightness curves corresponding to the multiple tissues in a magnetic resonance image generated using the random scan sequence.

19. The device as claimed in claim 18, wherein the computer is configured to determine whether the differentiation-indicating value between any two of the multiple tissues is less than a set threshold; and if the differentiation-indicating value of the any two tissues is less than the set threshold, to determine that in one image, the differentiation of the two brightness curves corresponding to the any two tissues is high.

20. The device as claimed in claim 11, wherein the computer is further configured to generate, based on the differentiation-indicating values of the multiple tissues, a differentiation-indicating matrix of multiple tissues, the element in row i and column j of the differentiation-indicating matrix of multiple tissues being the differentiation-indicating value of the $i^{th}$ tissue and the $j^{th}$ tissue.

* * * * *